United States Patent
Allard

(10) Patent No.: US 6,174,518 B1
(45) Date of Patent: Jan. 16, 2001

(54) PHOTOPROTECTIVE/COSMETIC COMPOSITIONS COMPRISING W/O/W STABLE TRIPLE EMULSIONS

(75) Inventor: Delphine Allard, Colombes (FR)

(73) Assignee: Societe L'Oreal S.A., Paris (FR)

( * ) Notice: Under 35 U.S.C. 154(b), the term of this patent shall be extended for 0 days.

(21) Appl. No.: 09/297,718

(22) PCT Filed: Sep. 1, 1998

(86) PCT No.: PCT/FR98/01876

§ 371 Date: Jul. 27, 1999

§ 102(e) Date: Jul. 27, 1999

(87) PCT Pub. No.: WO99/13853

PCT Pub. Date: Mar. 25, 1999

(30) Foreign Application Priority Data

Sep. 16, 1997 (FR) .................................................. 97 11494

(51) Int. Cl.[7] .............................. A61K 7/42; A61K 7/44; A61K 31/74; A61K 7/00

(52) U.S. Cl. .......................... 424/59; 424/60; 424/78.08; 424/400; 424/401; 514/937; 514/938; 514/940; 514/943

(58) Field of Search ................................ 424/59, 60, 400, 424/401, 78.08; 514/937, 938, 940, 943

(56) References Cited

FOREIGN PATENT DOCUMENTS

| | | |
|---|---|---|
| 0 507 693 | 10/1992 | (EP) . |
| 0 614 660 | 9/1994 | (EP) . |
| 95 17956 | 7/1995 | (WO) . |

OTHER PUBLICATIONS

Base De Donnés "Chemical Abstracts", Serveur: STN, Abrége 118: 219 475, Colombus, OH, USA; & JP 05 009 107 A (Noevir K.K.) Jan. 19, 1993, XP002083037.

*Primary Examiner*—Shelley A. Dodson
(74) *Attorney, Agent, or Firm*—Burns, Doane, Swecker & Mathis, L.L.P.

(57) ABSTRACT

The present invention relates to a cosmetic or dermatological emulsion of the water/oil/water (W/O/W) type, characterized in that it comprises:
(a) an external aqueous phase and
(b) a non-continuous fatty phase constituting, with an internal aqueous phase, a water/oil (W/O) primary emulsion, the said fatty phase comprising, as lipophilic emulsifier, at least one block copolymer composed of a polymer block derived from a monohydroxycarboxylic acid and of a polymer block derived from an alkylglycol or from a polyalkylene glycol;
(c) at least one photoprotective system capable of screening out UV (UV-A and/or UV-B) radiation.

The invention also relates to its uses in and for the manufacture of cosmetic or dermatological compositions for the photoprotection of the skin or hair.

35 Claims, No Drawings

PHOTOPROTECTIVE/COSMETIC COMPOSITIONS COMPRISING W/O/W STABLE TRIPLE EMULSIONS

BACKGROUND OF THE INVENTION

1. Technical Field of the Invention

The present invention relates to cosmetic or dermatological triple emulsions of the water/oil/water type comprising a non-continuous fatty phase comprising, as water/oil emulsifier, at least one block copolymer composed of a polymer block derived from a monohydroxycarboxylic acid and of a polymer block derived from an alkylglycol or from a polyalkylene glycol and a photoprotective system capable of screening out UV (UV-A and/or UV-B) radiation.

2. Description of the Prior Art

It is known that light radiation with wavelengths of between 280 nm and 400 nm makes it possible to tan the human epidermis and that radiation with wavelengths of between 280 nm and 320 nm, known under the name of UV-B radiation, causes erythemas and cutaneous burns which can be harmful to the development of a natural tan; this UV-B radiation must therefore be screened out.

It is also known that UV-A radiation with wavelengths of between 320 nm and 400 nm, which causes tanning of the skin, can induce a detrimental change in the latter, in particular in the case of sensitive skin or of skin continually exposed to solar radiation. UV-A radiation causes in particular a loss in elasticity of the skin and the appearance of wrinkles, resulting in premature ageing. It promotes the triggering of the erythemal reaction or accentuates this reaction in some subjects and can even be the source of phototoxic or photoallergic reactions. It is therefore desirable also to screen out UV-A radiation.

According to the invention, the term "photoprotective system capable of screening out UV radiation" is understood to denote generally any compound or any combination of compounds which, by mechanisms known per se of absorption and/or of reflection and/or of scattering of UV-A and/or UV-B radiation, makes it possible to prevent the said radiation from coming into contact, or at least to limit the contact, with a surface (skin, hair) on which this or these compounds have been applied. In other words, the compounds targeted by the present invention are simultaneously photoprotective organic screening agents which absorb UV radiation and inorganic (nano)pigments which scatter and/or reflect UV radiation, and their mixtures.

Numerous cosmetic and/or dermatological compositions intended for the photoprotection (UV-A and/or UV-B) of the skin have been provided to date.

These anti-sun compositions are fairly often provided in the form of an emulsion of oil-in-water type (that is to say, a cosmetically and/or dermatologically acceptable vehicle composed of a continuous aqueous dispersing phase and of a non-continuous fatty disperse phase) or water-in-oil type (aqueous phase dispersed in a continuous fatty phase) which comprises, at various concentrations, one or more lipophilic and/or hydrophilic conventional organic screening agents capable of selectively absorbing harmful UV radiation, these screening agents (and their amounts) being selected according to the desired sun protection factor (the sun protection factor (SPF) being expressed mathematically by the ratio of the irradiation time necessary to reach the erythematogenic threshold with the UV screening agent to the time necessary to reach the erythematogenic threshold without the UV screening agent). In such emulsions, the hydrophilic screening agents are present in the aqueous phase and the lipophilic screening agents are present in the fatty phase.

Anti-sun compositions in the form of an emulsion of oil-in-water or water-in-oil type can comprise inorganic pigments and/or nanopigments (that is to say, pigments for which the mean size of the primary particles generally does not exceed 100 nm) based on metal oxides and in particular on titanium oxide. They are increasingly sought after due to the fact that the latter substances, when they are used in combination with conventional UV screening agents (mainly organic compounds capable of absorbing harmful radiation), make it possible to obtain very high protection factors. These nanopigments can be present both in the aqueous phase of the emulsion and in its fatty phase.

Oil-in-water emulsions are generally better appreciated by the consumer than water-in-oil emulsions, in particular due to their pleasant feel (similar to water) and their presentation in the form of a non-greasy milk or cream; however, they also more readily lose their effectiveness with regard to UV protection as soon as they come into contact with water; this is because hydrophilic screening agents, in particular acidic screening agents, disappear in water, by bathing in the sea or in a swimming pool, under a shower or when taking part in water sports; thus, anti-sun compositions which comprise them, alone or in combination with lipophilic screening agents, no longer contribute the desired initial protection as soon as the substrate (skin or hair) on which they have been applied comes into contact with water, this loss in protection factor by removal in water of the hydrophilic screening agent being all the more marked in that the lipophilic-hydrophilic screening combination present in the composition is synergistic with regard to the sun protection factor.

It is possible to have available anti-sun compositions exhibiting improved SPFs and an improved resistance to water by employing water-in-oil emulsions. This is because a hydrophilic screening agent is more persistent towards water within a water-in-oil emulsion than within an oil-in-water emulsion. However, as was indicated above, such compositions are still not entirely satisfactory insofar as they leave, after application, a feeling of greasiness which is particularly unpleasant for the user.

Thus, the need still remains as regards being able to have available anti-sun compositions which can equally well comprise hydrophilic screening agents, lipophilic screening agents and nanopigments for which the SPF would be high, stable over time and resistant to water, whatever the hydrophilic and/or lipophilic screening agents and/or the nanopigments used, and for which the cosmetic performance would be comparable with that obtained with conventional oil/water emulsions.

Other types of emulsions, known as multiple emulsions, of the water/oil/water (W/O/W) or oil/water/oil (O/W/O) type are known in the prior art. Use is preferably made, among multiple emulsions, of emulsions with an external aqueous phase, namely W/O/W emulsions, which combine the advantages of freshness on application, contributed by the water present in the external aqueous phase, and of comfort, contributed by a relatively large amount of oil. In particular, provision has been made, in the document WO-A-94/22414, for a process for the preparation of W/O/W multiple emulsions which consists in preparing a W/O emulsion comprising a glyceryl fatty acid ester as W/O emulsifier and in dispersing this emulsion in an aqueous phase in the presence of an O/W emulsifier chosen from oxyethylenated fatty alcohols and oxyethylenated sterols.

The term "W/O emulsifier" is understood to mean, within the meaning of the present invention and in the text which follows, any compound having emulsifying properties making possible the preparation of water-in-oil emulsions.

The term "O/W emulsifier" is understood to mean, within the meaning of the present invention and in the text which follows, any compound having emulsifying properties making possible the preparation of oil-in-water emulsions.

Unfortunately, the stability of the emulsions obtained according to this document is insufficient to satisfy the requirements of commercial products, in particular on storage at high temperatures, for example greater than 40° C. Such an instability can result in a W/O emulsion, resulting in a loss of the qualities of the multiple emulsion, in particular its quality of freshness on application, since the external phase is no longer an aqueous phase. This multiple emulsion can also be converted into an O/W emulsion, which is often unstable with phase separation into an oil and water. Moreover, these emulsions require a choice of specific oils in large amounts which are not very emollient and are not always well tolerated by the skin and can cause irritation.

Cosmetic W/O/W triple emulsions comprising a W/O primary emulsion comprising, in the non-continuous fatty phase, as W/O emulsifier, a polyoxyethylenated (2.5 mol of ethylene oxide) and polyoxypropylenated (1.5 mol of propylene oxide) derivative of a mixture of glycerol and sorbitol esters of hydroxystearic and isostearic acids, sold under the trade name Arlacel 780 by the Company ICI, are also known in Application EP-A-691,839.

Applicant has found that emulsions of this type could not be used in the field of the protection of the skin and hair against UV radiation, in particular against solar radiation, insofar as they were unstable on storage in the presence of hydrophilic screening agents and/or of lipophilic screening agents and/or of nanopigments based on metal oxides in their composition.

SUMMARY OF THE INVENTION

Applicant has discovered, surprisingly and unexpectedly, that certain W/O/W multiple emulsions, comprising, in the external aqueous phase, a W/O primary emulsion comprising, in the non-continuous fatty phase, as W/O emulsifier, a block copolymer composed of a polymer block derived from a monohydroxycarboxylic acid and of a polymer block derived from an alkylglycol or from a polyalkylene glycol, could, on the one hand, equally well comprise hydrophilic screening agents, lipophilic screening agents and nanopigments, without exhibiting the stability problems recalled above, and, on the other hand, could result in high SPFs which are stable over time, whatever the hydrophilic and/or lipophilic screening agents and/or nanopigments used.

Applicant has also discovered that these same specific W/O/W multiple emulsions made it possible not only to obtain anti-sun compositions with a cosmetic performance comparable to that generally obtained with a conventional anti-sun composition in the form of an oil/water emulsion but also exhibited an improved persistence towards water.

Applicant has also discovered that these same W/O/W multiple emulsions could comprise a large variety of oils constituting the fatty phase of the said emulsions which are well tolerated by the skin, do not cause irritation and contribute the cosmetic advantages of an emulsion with an external aqueous phase.

These discoveries are at the basis of the present invention.

The subject-matter of the present invention is a triple cosmetic or dermatological emulsion of the W/O/W type, characterized in that it comprises:
(a) an external aqueous phase and
(b) a non-continuous fatty phase constituting, with an internal aqueous phase, a W/O primary emulsion, the said fatty phase comprising, as W/O emulsifier, at least one block copolymer composed of a polymer block derived from a monohydroxycarboxylic acid and of a polymer block derived from an alkylglycol or from a polyalkylene glycol;
(c) at least one photoprotective system capable of screening out UV (UV-A and/or UV-B) radiation.

The term "cosmetic or dermatological emulsion", within the meaning of the present invention and in the text which follows, is understood to mean any emulsion in which the external and internal aqueous phases and the non-continuous fatty phase are composed of substances which are cosmetically or dermatologically acceptable for a topical application to human keratinous substances, including the skin, hair, eyelashes, eyebrows, lips, nails or mucous membranes.

Another subject-matter of the present invention is a cosmetic treatment process for the protection of the skin and/or hair against ultraviolet radiation, in particular solar radiation, which consists in applying, to the latter, an effective amount of a composition as defined above.

Another subject-matter of the present invention is the use of the composition as defined above as, or for the manufacture of, cosmetic compositions for the protection of the skin and/or hair against ultraviolet radiation, in particular solar radiation.

Other characteristics, advantages and aspects of the present invention will become apparent on reading the detailed description which will follow.

DETAILED DESCRIPTION OF BEST MODE AND SPECIFIC/PREFERRED EMBODIMENTS OF THE INVENTION

According to the present invention, the W/O emulsifiers of the block copolymer type composed of a polymer block derived from a monohydroxycarboxylic acid and of a polymer block derived from an alkylglycol or from a polyalkylene glycol correspond to the following general formula:

A-B-A  (I)

in which:
A denotes an oil-soluble monohydroxycarboxylic acid residue having a molecular weight of at least 500 of following formula:

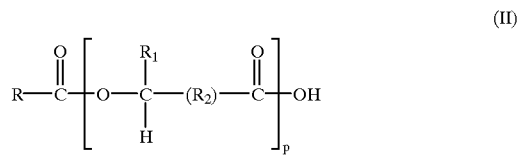

(II)

in which:
R is a hydrogen or a substituted or unsubstituted monovalent hydrocarbon-comprising group;
$R_1$ is a hydrogen or a monovalent $C_1$–$C_{24}$ hydrocarbon-comprising group;
$R_2$ is a divalent $C_1$–$C_{24}$ hydrocarbon-comprising group;
p is a number from 1 to 200;

B denotes a divalent residue of an alkylglycol or of a polyalkylene glycol having a molecular weight of at least 500 and corresponding to the following formula:

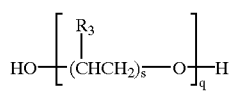
(III)

in which:
the $R_3$ radicals, which are identical or different, represent hydrogen or a $C_1$–$C_4$ alkyl radical;
q is a number from 1 to 100;
s is a number from 1 to 17.

R preferably denotes a linear or branched alkyl radical comprising up to 25 carbon atoms and more preferably a linear chain comprising from 12 to 24 carbon atoms, preferably from 14 to 20 carbon atoms, for example derived from oleic, palmitic or stearic acid.

The units comprising the $R_1$ and $R_2$ radicals preferably constitute a linear chain comprising from 12 to 24 carbon atoms, preferably from 14 to 20 carbon atoms, and can denote a residue of hydroxyoleic acid, hydroxypalmitic acid or hydroxystearic acid.

The alkylene glycol and/or polyalkylene glycol groups can be chosen, for example, from ethylene glycol, propylene glycol or other $C_4$–$C_5$ alkylglycols. B more particularly denotes a polyethylene glycol or 1,4-butanediol residue.

The block copolymers of formula (I) are known per se and are disclosed in particular in Patents GB 1,469,591 and U.S. Pat. No. 4,203,877 and Patent Application WO 96/07689. These same documents disclose their methods of preparation.

According to a particularly preferred form of the invention, use will be made, in the non-continuous fatty phase in the multiple emulsions, of a block copolymer corresponding to the formula (I) in which A denotes the residue of a poly(12-hydroxystearic acid) chain which is terminated by a stearic acid group and B denotes a polyethylene glycol residue; the polyethylene glycol blocks of the said emulsifying copolymer comprise from 4 to 50 mol of ethylene oxide and more preferably from 20 to 40 mol of ethylene oxide.

Use will more particularly be made of the block copolymer sold under the name Arlacel P135 by the company ICI, the INCI name of which is PEG-30 Dipolyhydroxystearate.

According to the invention, the W/O emulsifier block copolymer is preferably present in an amount ranging from 0.5 to 10% by weight, preferably from 2 to 5% by weight.

The non-continuous fatty phase of the multiple emulsions according to the invention is composed of fatty substances chosen from silicone oils, waxes, gums or resins and their mixtures commonly used for the preparation of emulsions employed in anti-sun compositions.

The term "oil" is understood to mean a compound which is liquid at room temperature. The term "wax" is understood to mean a compound which is solid or substantially solid at room temperature and for which the melting point is generally greater than 35° C.

Mention may be made, as oils, of, for example, mineral oils, such as isoparaffins; vegetable oils (sweet almond oil, macadamia oil, blackcurrant seed oil, jojaba oil); synthetic oils, such as perhydrosqualene, fatty alcohols, acids or esters (octyl palmitate, isopropyl lanolate, triglycerides, including those of capric/caprylic acids), or oxyethylenated or oxypropylenated fatty esters and ethers; silicone oils (cyclomethicone, polydimethyl-siloxanes or PDMS) or fluorinated oils; or poly-alpha-olefins, such as hydrogenated or non-hydrogenated polydecenes or hydrogenated or non-hydrogenated polyisobutylenes.

Mention may be made, as waxy compounds, of paraffin wax, carnauba wax, beeswax or hydrogenated castor oil.

The non-continuous fatty phase is advantageously present in an amount ranging from 5 to 40% by weight and more preferably from 10 to 30% by weight with respect to the total weight of the triple emulsion.

The W/O primary emulsion according to the invention is preferably present in an amount ranging from 40 to 80% by weight and more preferably from 50 to 80% by weight with respect to the total weight of the triple emulsion.

According to the invention, the external aqueous phase preferably comprises one or more O/W emulsifiers. Mention may be made of those comprising an oxyethylenated group, such as oxyethylenated fatty alcohols, oxyethylenated sterols and their mixtures. Use might be made of other types of O/W emulsifiers, in particular of those having an HLB (Hydrophilic Lipophilic Balance) of greater than 10, such as oxyethylenated nonylphenols, oxyethylenated and/or oxypropylenated block polymers, such as Poloxamers, or sorbitan fatty esters.

The oxyethylenated fatty alcohols advantageously have a fatty chain comprising from 16 to 22 carbon atoms and preferably comprise from 20 to 50 and better still from 20 to 30 mol of ethylene oxide. Mention may be made, as oxyethylenated fatty alcohols which can be used according to the invention, of, for example, the cetyl/stearyl alcohol mixture oxyethylenated with 30 mol of ethylene oxide (CTFA name: Ceteareth-30).

The oxyethylenated sterols preferably comprise from 10 to 40 and better still from 25 to 30 mol of ethylene oxide. Mention may be made, as oxyethylenated sterols, of, for example, soya sterol oxyethylenated with 25 mol of ethylene oxide (CTFA name: PEG-25 Soya sterol).

Use will more particularly be made of the polyoxyethylene/polyoxypropylene block copolymer known under the CTFA name Poloxamer 407 and sold under the trade name Synperonic PE/F 127 by the Company ICI.

The O/W emulsifiers are preferably present in an amount ranging from 0.1 to 10% by weight and preferably from 0.5 to 5% by weight with respect to the total weight of the emulsion.

The process used to prepare the multiple emulsion according to the invention is identical to the process disclosed in the document WO-A-94/22414. It consists in mixing the oil or oils and the W/O emulsifier and in introducing the internal aqueous phase into the mixture with vigorous stirring and in then introducing the primary emulsion obtained, with stirring, into the external aqueous phase preferably comprising at least one O/W emulsifier, until the W/O/W emulsion is obtained.

According to the invention, the photoprotective system is composed of one or more hydrophilic UV-absorbing organic screening agents and/or one or more lipophilic UV-absorbing organic screening agents and/or one or more inorganic (nano)pigments.

According to the invention, the hydrophilic organic screening agents can be incorporated in the internal aqueous phase of the primary W/O emulsion and/or in the external aqueous phase of the triple emulsion. They are chosen in particular from benzophenone derivatives, p-aminobenzoic acid derivatives or camphor derivatives, or alternatively from benzimidazole derivatives.

Mention may be made, as hydrophilic organic screening agents which can be particularly used in the present invention, of benzene-1,4-di(3-methylidene-10-camphorsulphonic acid) and 2-phenylbenzimidazole-5-sulphonic acid, sold under the trade name "Eusolex 232" by the company Merck.

The hydrophilic organic screening agent or agents can be present in the final composition according to the invention at a content which can vary from 0.1 to 20%, preferably from 0.2 to 10%, by weight with respect to the total weight of the composition.

According to the invention, the lipophilic organic screening agents can be present in the non-continuous fatty phase of the triple emulsion. They can be chosen from dibenzoylmethane derivatives, benzimidazole derivatives, cinnamic derivatives, salicylic derivatives, camphor derivatives, triazine derivatives, benzophenone derivatives, β,β-diphenylacrylate derivatives, p-aminobenzoic acid derivatives, or the screening polymers and the screening silicones disclosed in Applications WO-93/04665 and WO-94/06404. Other examples of organic screening agents are given in Patent Application EP-A-0487404.

Mention may be made, as lipophilic organic screening agents which can be particularly used in the present invention, of 4-tert-butyl-4'-methoxydibenzoylmethane, sold under the trade name "Parsol 1789" by the company Givaudan, octyl methoxycinnamate, sold under the trade name "Parsol MCX" by Givaudan, and 2-ethylhexyl α-cyano-β,β-diphenylacrylate, sold under the trade name "Uvinul N539" by the company BASF.

The lipophilic organic screening agent or agents can be present in the final composition according to the invention at a content which can vary from 0.5 to 30%, preferably from 0.5 to 20%, by weight with respect to the total weight of the composition.

A second category of photoprotective agents which is particularly well suited to the multiple emulsions according to the invention is that of pigments. Use is preferably made of coated or non-coated metal oxide inorganic nanopigments (mean size of the primary particles: generally between 5 nm and 100 nm, preferably between 10 and 50 nm), such as, for example, titanium oxide (amorphous or crystalline in rutile and/or anatase form), iron oxide, zinc oxide, zirconium oxide or cerium oxide nanopigments, which are all photoprotective agents well known per se which act by physically blocking (reflecting and/or scattering) UV radiation. Conventional coating agents are, furthermore, alumina and/or aluminium stearate or silicones. Such coated or non-coated metal oxide nanopigments are disclosed in particular in Patent Applications EP-A-0,518,772 and EP-A-0,518,773.

The inorganic (nano)pigment or (nano)pigments can be present in the compositions according to the invention at a content of between 0.1% and 30%, preferably from 0.5% to 10%, by weight with respect to the total weight of the composition.

The compositions according to the invention can also comprise thickeners.

The thickeners can be chosen in particular from crosslinked polyacrylic acids, polyacrylic acids comprising a fatty chain, or modified or non-modified guar gums and celluloses, such as hydroxypropylated guar gum, methylhydroxyethylcellulose and hydroxypropylmethyl cellulose.

The thickener or thickeners can be present in the final composition according to the invention at a content which can range from 0.1 to 10%, preferably from 0.1 to 5%, by weight with respect to the total weight of the composition.

The compositions according to the invention can also comprise agents for the artificial tanning and/or browning of the skin (self-tanning agents), such as, for example, dihydroxyacetone (DHA).

The compositions in accordance with the present invention can additionally comprise conventional cosmetic and/or dermatological adjuvants chosen in particular from organic solvents, softeners, antioxidants, agents for combating free radicals, opacifiers, stabilizers, emollients, α-hydroxy acids, antifoaming agents, moisturizing agents, vitamins, fragrances, preservatives, surfactants, fillers, sequestering agents, polymers, propellants, basifying or acidifying agents, dyes or any other ingredient commonly used in the cosmetics and/or dermatological field, in particular for the manufacture of anti-sun compositions in the form of emulsions.

Of course, a person skilled in the art will take care to choose the optional additional compound or compounds mentioned above and/or their amounts so that the advantageous properties intrinsically attached to the multiple emulsions in accordance with the invention are not, or not substantially, detrimentally affected by the envisaged addition or additions.

Concrete but in no way limiting examples illustrating the invention will now be given.

EXAMPLES

EXAMPLE 1

Anti-Sun Composition in the Form of a W/O/W Emulsion

| Non-continuous fatty phase: | |
|---|---|
| Block copolymer of formula (I), sold under the name Arlacel P135 by ICI | 2.4% by weight |
| Isohexadecane | 6.6% |
| Stearyl alcohol oxypropylenated with 15 mol of propylene oxide | 3.3% |
| Mixture of capric acid and caprylic acid triglycerides | 3.3% |
| Octyl methoxycinnamate, sold under the name "Parson MCX" by Givaudan | 5.0% |
| Internal aqueous phase: | |
| Benzene-1,4-di(3-methylidene-10-camphorsulphonic acid) | 1% |
| Triethanolamine | 0.56% |
| Preservatives | 0.72% |
| Water | 37.12% |
| External aqueous phase: | |
| Benzene-1,4-di(3-methylidene-10-camphorsulphonic acid) | 1% |
| POE/POP Block copolymer (CTFA name: Poloxamer 407), sold under the name Synperonic PE/F 127 by ICI | 2.0% |
| Triethanolamine | 0.56% |
| Thickener | 0.7% |
| Preservatives | 1.2% |
| Water q.s. for | 100% |

The composition obtained remains stable on storage after 2 months at room temperature and at temperatures greater than 40° C.

EXAMPLE 2

Comparative: Not According to the Invention

An anti-sun emulsion of the W/O/W type is prepared which is identical to that of Example 1 but in which the product Arlacel P135 has been replaced by a polyoxyethylenated (2.5 mol of ethylene oxide) and polyoxypropylenated (1.5 mol of propylene oxide) derivative of a mixture of glycerol and sorbitol esters of hydroxystearic and isostearic acids sold under the trade name Arlacel 780 by the Company ICI. The concentration of the W/O emulsifier is identical to that used in Example 1. It is observed that the emulsion is unstable.

EXAMPLE 3

Comparative: Not According to the Invention

A conventional anti-sun O/W emulsion is prepared which has the following composition:

| | |
|---|---|
| Arlacel 165 (emulsifier) | 2% |
| Conventional coemulsifiers | 3.75% |
| Silicone | 10.5% |
| Conventional fatty substances | 10.5% |
| Moisturizer | 8% |
| Thickener/gelling agent | 0.4% |
| Parsol MCX | 5% |
| Benzene-1,4-di(3-methylidene-10-camphorsulphonic acid) | 2% |
| Triethanolamine | 1.82% |
| Preservative, water q.s. for | 100% |

1) Evaluation of the persistence towards water of the compositions of Examples 1 and 3

For each of the formulations of Examples 1 and 3 thus prepared, the resistance to water of the sun protection factor (SPF) attached to it was subsequently determined.

The sun protection factor was measured according to the following method (in vivo): these formulations were applied, at the rate of 2 mg of product/cm² of skin, to the backs of 5 human models and then the protected and unprotected skin regions were simultaneously subjected to the action of a solar simulator sold under the name of "Xenon Multiport WG 320-UG 11"; the sun protection factor (SPF) was then calculated mathematically by the ratio of the irradiation time necessary to reach the erythematogenic threshold with the UV screening agent (protected region) to a time necessary to reach the erythematogenic threshold without a UV screening agent (unprotected region).

According to this method, the SPF of each formulation is determined on skin regions which have been treated with each of them and which have not been subjected to bathing.

At the same time, the SPF of each formulation is also determined on skin regions which have been treated with each of them and which have been subjected to two bathings, each bathing lasting 20 minutes and the two bathings being separated by a period of 20 minutes.

The variation in the SPF of each formulation (expressed as a percentage) with bathing and without bathing is subsequently calculated, which corresponds to the percentage of persistence towards water.

The results are given with a 95% confidence interval in the table below:

| | % persistence |
|---|---|
| Example 1 (invention) | 76.8 ± 15.8 |
| Example 3 (comparative) | 46.9 ± 14.2 |

These results clearly show that, with an identical screening system, the W/O/W triple emulsion of Example 1 in accordance with the present invention exhibits a better persistence towards water than the conventional O/W emulsion of Example 3.

2) Evaluation of the Cosmetic Properties of the Compositions of Examples 1 and 3

A sensory test is carried out on a panel of 10 people by applying each of the emulsions of Examples 1 and 3 at the rate of 0.2 g on the skin of each forearm. The following criteria were studied:
Ease of application
Greasiness
Stickiness
Speed of drying
Smoothness The 10 people considered that the W/O/W triple emulsion of Example 1 in accordance with the invention contributed cosmetic properties analogous to those of the conventional W/O emulsion of Example 3.

What is claimed is:

1. A cosmetic/dermatological water/oil/water (W/O/W) stable triple emulsion, which comprises (a) an external aqueous phase, (b) a non-continuous fatty phase constituting, together with an internal aqueous phase, a water/oil (W/O) primary emulsion, said fatty phase including a W/O emulsifier which comprises at least one block copolymer, one polymer block of which comprising the polymerizate of a monohydroxycarboxylic acid and another polymer block of which comprising the polymerizate of an alkylglycol or polyalkylene glycol, and (c) at least one UV-photoprotecting active agent.

2. The W/O/W stable triple emulsion as defined by claim 1, said at least one block copolymer having the general formula (1):

A-B-A            (I)

in which A is an oil-soluble monohydroxycarboxylic acid residue having a molecular weight of at least 500 and the following structural formula (II):

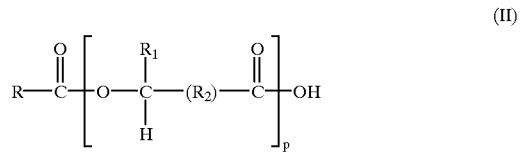

(II)

in which R is a hydrogen atom or a substituted or unsubstituted monovalent hydrocarbon-containing radical; $R_1$ is a hydrogen atom or a monovalent $C_1$–$C_{24}$ hydrocarbon-containing radical; $R_2$ is a divalent $C_1$–$C_{24}$ hydrocarbon-containing radical; p is a number ranging from 1 to 200; and B is a divalent residue of an alkylglycol or a polyalkylene glycol having a molecular weight of at least 500 and having the following structural formula (III):

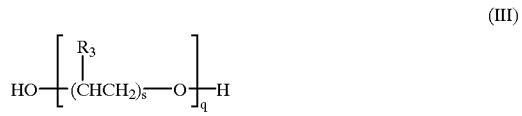

(III)

in which the radicals $R_3$, which may be identical or different, are each a hydrogen atom or a $C_1$–$C_4$ alkyl radical; q is a number ranging from 1 to 100; and s is a number ranging from 1 to 17.

3. The W/O/W stable triple emulsion as defined by claim 2, wherein formula (II), R is a linear or branched alkyl radical having up to 25 carbon atoms.

4. The W/O/W stable triple emulsion as defined by claim 3, wherein formula (II), R is a linear alkyl radical having from 12 to 24 carbon atoms.

5. The W/O/W stable triple emulsion as defined by claim 4, wherein formula (II), R is a linear alkyl radical having from 14 to 20 carbon atoms.

6. The W/O/W stable triple emulsion as defined by claim 2, wherein formula (II), $R_1$ and $R_2$ are each a hydrocarbyl radical having from 12 to 24 carbon atoms.

7. The W/O/W stable triple emulsion as defined by claim 6, wherein formula (II), $R_1$ and $R_2$ are each a hydrocarbyl radical having from 14 to 20 carbon atoms.

8. The W/O/W stable triple emulsion as defined by claim 2, wherein formula (I), B is a divalent residue of a polyethylene glycol.

9. The W/O/W stable triple emulsion as defined by claim 8, wherein formula (I), A is the residue of a poly(12-hydroxystearic acid) terminated by a stearic acid group.

10. The W/O/W stable triple emulsion as defined by claim 8, said divalent residue of a polyethylene glycol comprising from 4 to 50 mol of ethylene oxide.

11. The W/O/W stable triple emulsion as defined by claim 10, said divalent residue of a polyethylene glycol comprising from 20 to 40 mol of ethylene glycol.

12. The W/O/W stable triple emulsion as defined by claim 1, comprising from 0.5% to 10% by weight of said W/O emulsifier.

13. The W/O/W stable triple emulsion as defined by claim 12, comprising from 2% to 5% by weight of said W/O emulsifier.

14. The W/O/W stable triple emulsion as defined by claim 1, comprising from 5% to 40% by weight of said non-continuous fatty phase.

15. The W/O/W stable triple emulsion as defined by claim 14, comprising from 10% to 30% by weight of said non-continuous fatty phase.

16. The W/O/W stable triple emulsion as defined by claim 1, comprising from 40% to 80% by weight of said W/O primary emulsion.

17. The W/O/W stable triple emulsion as defined by claim 16, comprising from 50% to 80% by weight of said W/O primary emulsion.

18. The W/O/W stable triple emulsion as defined by claim 1, said external aqueous phase comprising at least one O/W emulsifier.

19. The W/O/W stable triple emulsion as defined by claim 1, comprising at least one hydrophilic UV-absorbing organic photoprotecting active agent.

20. The W/O/W stable triple emulsion as defined by claim 19, said at least one hydrophilic UV-absorbing organic photoprotecting active agent comprising a benzophenone compound, p-aminobenzoic acid compound, camphor compound and/or benzimidazole compound.

21. The W/O/W stable triple emulsion as defined by claim 20, said at least one hydrophilic UV-absorbing organic photoprotecting active agent comprising benzene-1,4-di(3-methylidene-10-camphorsulfonic acid) or 2-phenylbenzimidazole-5-sulfonic acid.

22. The W/O/W stable triple emulsion as defined by claim 19, comprising from 0.1% to 20% by weight of said at least one hydrophilic UV-absorbing organic photoprotecting active agent.

23. The W/O/W stable triple emulsion as defined by claim 1, comprising at least one lipophilic UV-absorbing organic photoprotecting active agent.

24. The W/O/W stable triple emulsion as defined by claim 23, said at least one lipophilic UV-absorbing organic photoprotecting active agent comprising a dibenzoylmethane compound, benzimidazole compound, cinnamic compound, salicylic compound, camphor compound, triazine compound, benzophenone compound, β-β-diphenylacrylate compound, p-aminobenzoic acid compound, UV-screening polymer and/or UV-screening silicone.

25. The W/O/W stable triple emulsion as defined by claim 24, said at least one lipophilic UV-absorbing organic photoprotecting active agent comprising 4-tert-butyl-4'-methoxydibenzoylmethane, octyl methoxycinnamate or 2-ethylhexyl α-cyano-β,β-dipenylacrylate.

26. The W/O/W stable triple emulsion as defined by claim 23, comprising from 0.5% to 30% by weight of said at least one lipophilic UV-photoprotecting active agent.

27. The W/O/W stable triple emulsion as defined by claim 1, comprising at least one inorganic UV-photoprotecting (nano)pigment.

28. The W/O/W stable triple emulsion as defined by claim 27, said at least one inorganic UV-photoprotecting (nano)pigment comprising a coated or uncoated metal oxide nanopigment.

29. The W/O/W stable triple emulsion as defined by claim 28, said at least one coated or uncoated metal oxide nanopigment comprising titanium oxide, iron oxide, zinc oxide, zirconium oxide and/or cerium oxide.

30. The W/O/W stable triple emulsion as defined by claim 27, comprising from 0.1% to 30% by weight of said at least one inorganic UV-photoprotecting (nano)pigment.

31. The W/O/W stable triple emulsion as defined by claim 30, comprising from 0.5% to 10% by weight of said at least one inorganic UV-photoprotecting (nano)pigment.

32. The W/O/W stable triple emulsion as defined by claim 1, further comprising an effective amount of at least one artificial tanning and/or browning agent for the skin.

33. A regime/regimen for protecting a human keratinous substrate against the deleterious effects of ultraviolet irradiation, comprising topically applying thereto a thus-effective amount of the W/O/W stable triple emulsion as defined by claim 1.

34. A regime/regimen for protecting human skin and/or hair against the deleterious effects of ultraviolet irradiation, comprising topically applying thereto a thus-effective amount of the W/O/W stable triple emulsion as defined by claim 1.

35. A regime/regimen for protecting human skin and/or hair against the deleterious effects of solar radiation, comprising topically applying thereto a thus-effective amount of the W/O/W stable triple emulsion as defined by claim 1.

* * * * *